United States Patent
Lepage

(10) Patent No.: US 8,519,702 B2
(45) Date of Patent: Aug. 27, 2013

(54) ORTHOGONAL EDDY CURRENT PROBE FOR MULTI-DIRECTIONAL INSPECTION

(75) Inventor: Benoit Lepage, Quebec (CA)

(73) Assignee: Olympus NDT Inc., Waltham, MA (US)

( * ) Notice: Subject to any disclaimer, the term of this patent is extended or adjusted under 35 U.S.C. 154(b) by 367 days.

(21) Appl. No.: 12/847,074

(22) Filed: Jul. 30, 2010

(65) Prior Publication Data
US 2012/0025816 A1 Feb. 2, 2012

(51) Int. Cl.
*G01N 27/82* (2006.01)

(52) U.S. Cl.
USPC .......................................... 324/240

(58) Field of Classification Search
USPC ................. 324/232, 238, 240, 242, 699
See application file for complete search history.

(56) References Cited

U.S. PATENT DOCUMENTS

| | | | | |
|---|---|---|---|---|
| 3,495,166 | A * | 2/1970 | O'Connor et al. | 324/238 |
| 4,825,166 | A * | 4/1989 | MacGugan | 324/346 |
| 6,377,040 | B1 * | 4/2002 | Hell | 324/240 |
| 6,734,668 | B2 * | 5/2004 | Hils et al. | 324/232 |
| 6,791,319 | B2 * | 9/2004 | Hiroshima | 324/240 |
| 7,042,411 | B2 * | 5/2006 | Yagi et al. | 343/788 |
| 7,560,920 | B1 * | 7/2009 | Ouyang et al. | 324/242 |
| 2010/0079157 | A1 * | 4/2010 | Wincheski et al. | 324/699 |

FOREIGN PATENT DOCUMENTS

| | | | | |
|---|---|---|---|---|
| GB | 2456583 | A | * | 7/2009 |
| JP | 2009069090 | A | * | 4/2009 |

OTHER PUBLICATIONS

Li Shu, et al., Study of pulse eddy current probes detecting cracks extending in all directions, Jul. 17, 2007, ElSeiver, p. 13-19.*
Hansen, J., The eddy current inspection method, Parts 1-4, May 2004, Insight, vol. 46, No. 5.*

* cited by examiner

*Primary Examiner* — Arleen M Vazquez
*Assistant Examiner* — Giovanni Astacio-Oquendo
(74) *Attorney, Agent, or Firm* — Ostrolenk Faber LLP

(57) ABSTRACT

An orthogonal eddy current probe with at least three coils, each of the coils is wound across the two facing sides of an at least six-sided right polygonal [b1] prism. At each time interval, two of the three coils are used as driver coils, being charged simultaneously with electric current driven in coherent directions to induce a combined eddy current and one of the coils is used as a receiver coil to sense the eddy current, with the combined eddy current to be orthogonal to the receiver coil. Each coil alternates to be one of the driver coils or the receiver coil at a predetermined switching sequence and a predetermined switching frequency during consecutive time intervals. The eddy current probe provides advantages of inspecting a test surface for flaws of any flaw orientation with one pass of scan, providing sufficient sensitivity and desirable noise cancellation in all directions.

16 Claims, 11 Drawing Sheets

ORTHOGONAL EDDY CURRENT PROBE FOR MULTI-DIRECTIONAL INSPECTION

FIELD OF THE INVENTION

The present invention relates to non-destructive testing and inspection systems (NDT/NDI), particularly to eddy current (EC) technology and eddy current probes with multi-directional sensitivity capabilities.

BACKGROUND OF THE INVENTION

Eddy current inspection is commonly used for non-destructive inspection purposes to detect flaws in surfaces of manufactured goods fabricated of a conductive material, such as bars, tubes, and other components for many industries such as automotive, aeronautic and energy, etc. Eddy current probes can be used with many configurations and/or inducing-sensing mode.

One of the most widely used EC probe configurations is the transmit-receive configuration. This configuration typically includes a driver coil and a receiver coil. For this configuraiton, the EC probe's driver coil is provided with alternative electrical excitation signals which generates an alternating electromagnetic field, resulting in a magnetic field on a test surface of a test object as the probe is moved along a path above the test surface. The magnetic field induces eddy currents on and near the surface of the test object fabricated of a conductive material. The eddy currents result in an electro-magnetic signal or response on and near the test surface, which is received by the receiver coil and further analysed by an EC instrument/system As the eddy current probe passes over an anomaly, a flaw or a discontinuity in the test object, the anomaly disrupts the eddy current and results in a received signal that is irregular or out-of-pattern in comparison to signals received from normal objects. The deviation in the signal is used to indicate the anomaly. The alteration of the reading of the receiver is detected by the acquisition and analysis unit.

Typically, transmit-receive eddy current probes presents "directional sensitivity", which means those EC probes are only effective to detect flaws that are approximately aligned with the "sensitive direction", which is the driver-receiver axis. However, many test objects include complex surfaces, some resulting from complex manufacturing processes which create complicated stress patterns. Stress regions are prone to develop flaws which are randomly oriented, not necessarily being aligned with the directional sensitivity of the probe.

If the orientation of the flaw differs slightly from the sensitive direction of the probe, the result is a detection of the flaw with a sensitivity lower than that from the same flaw which is aligned with the probe. For example, a transmit-receive probe dedicated to 0 degree flaw detection, could be able to detect flaws at +/−20 deg but with a significantly smaller signal amplitude at the outer-boundary of the +/−20 deg. As a result, a shallow flaw perfectly aligned with the most sensitive orientation of the probe could be detected with a signal stronger than a deep flaw with an orientation slightly different from the directional sensitivity of the probe.

Usually the gravity of a flaw is defined by its estimated depth. As widely practiced, the decision to accept or reject an object being tested depends on the estimated depth of the flaw. If a reading of a flawing is larger than the acceptable limit, the object is rejected. However, if more than one flaw direction is anticipated and the reading of the flaw marginally meets or is within the acceptable limit, the user has to decide 1) to accept an otherwise rejectable test object, since the reading does not show the real depth of the flaw due the mis-alignment of the flaw with the sensitive direction, or 2) reject an otherwise acceptable object assuming the true depth is larger than it is measured. A third option is to repeatedly scan the component to detect flaws in different orientations, but the repeated scanning makes this process laborious and time consuming.

A special type of transmit-receive eddy current probe having two directional sensitivity, is known as an "orthogonal probe". It is built with two coils wound orthogonally to each other on a non-conductive cube or a cross-shaped core. One of the coils is a "driver", which is used to induce eddy current on the test surface, and the other is a "receiver", which is used to sense the induced eddy current on the test surface. An important aspect of the orthogonal probe is that the fact that the driver and the receiver being perpendicular to each other decouples the driver magnetic field from the receiver, thereby reducing the sensitivity of the receiver to surface noise that does not represent a flaw.

U.S. Pat. No. 3,495,166 is incorporated by reference as the example for background art pertaining to the orthogonal EC probe herein mentioned.

In accordance with an important feature of the background art, the orthogonal EC probe includes field-sensing means for sensing fields produced by EC's in two regions having substantially the same spatial relation to a surface of the part and having a substantial angle therebetween with detector means being provided for detecting differences between the fields produced in the two regions. It should be noted that the sensing regions of the field-sensing means are orthogonal to the emitted magnetic field regions of field-producing means. Accordingly, in the absence of a defect that will disrupt the direction of the EC flow imparted by the field-producing means, the magnetic field resulting from the EC flow will also be orthogonal to the field-sensing means and will consequently not be sensed. With this arrangement, a high degree of sensitivity is obtained with respect to flaws having different orientations with respect to the sensing regions, while being insensitive to changes in a) conductivity, b) permeability, c) irregular surface finishes and d) to changes in the spacing of the part. This insensitivity stems from the fact that properties a, b, c and d affect predominantly the magnitude of the EC flow and resulting magnetic field, but not the direction.

As can be seen that orthogonal probes used with different inducing mode can therefore provide inspection to flaw orientations 0 deg, +/−45 deg, +/−90 deg, and with desirable insensitivity to noises such as conductivity, permeability, etc. However, this design still falls short of providing scanning sensitivity to flaws with any flaw orientation around 360 deg.

The inability or the inaccuracy to detect flaws in all orientation hinders any eddy current system from achieving higher performance and causes safety concerns. Repeating runs of scans falls short of being less efficient and cost effective.

SUMMARY OF THE INVENTION

The invention disclosed herein solves the problems related to the effort in using eddy current systems to effectively detect flaws of all orientations, while the existing transmit-receive and orthogonal probes present the aforementioned drawbacks, such as inability or lacking the accuracy of inspecting flaws with all flaw orientations.

Note that the terms "probe", "transducer", and "sensor" used herein may be used interchangeably. "Emitter", "driver" and "driver coil" are herein used interchangeably. "Receiver" and "sensing coil" are herein used interchangeably.

Accordingly, it is a general objective to provide a multi-directional eddy current probe that can effectively detect flaws in multiple directions with one run of scaning the test object.

In addition, it is another objective to provide a multi-directional eddy current probe that is able to detect flaws in any orientation with a sufficient EC signal amplitude in substantially all directions.

It is another objective to provide a multi-directional eddy current probe, while being able to inspect flaws of all orientation, that has desirable noise cancellation and is insensitive to changes in conductivity, permeability, irregular surface finishes and in the spacing of the part, inheriting the advantages of existing orthogonal EC probes.

It is yet another objective to provide an eddy current probe capable of providing informations on the flaw orientation, not only the flaw size and depth.

The improved orthogonal eddy current probe includes at least three coils; each of the coils is wound across the two facing sides of an at least six-sided right polygonal prism, such as a hexagonal core. At each time interval, two of the three coils are used as driver coils, being charged simultaneously with electric current driven in coherent directions to induce a combined eddy current and one of the coils is used as a receiver coil to sense the eddy current.

Besides achieving a combined eddy current of the two coils, another important aspect of present disclosure is that the combined eddy current is orthogonal to the receiver coil.

Each coil alternates to be one of the driver coils or the receiver coils at a predetermined switching sequence and a predetermined switching frequency during consecutive time intervals.

The advantages of the multi-directional eddy current probe will be obvious with the disclosure in terms of capability of inspecting a test surface for flaws of any flaw orientation with sufficient sensitivity and desirable noise cancellation in all directions.

DETAILED DESCRIPTION OF THE INVENTION

Figure 1:
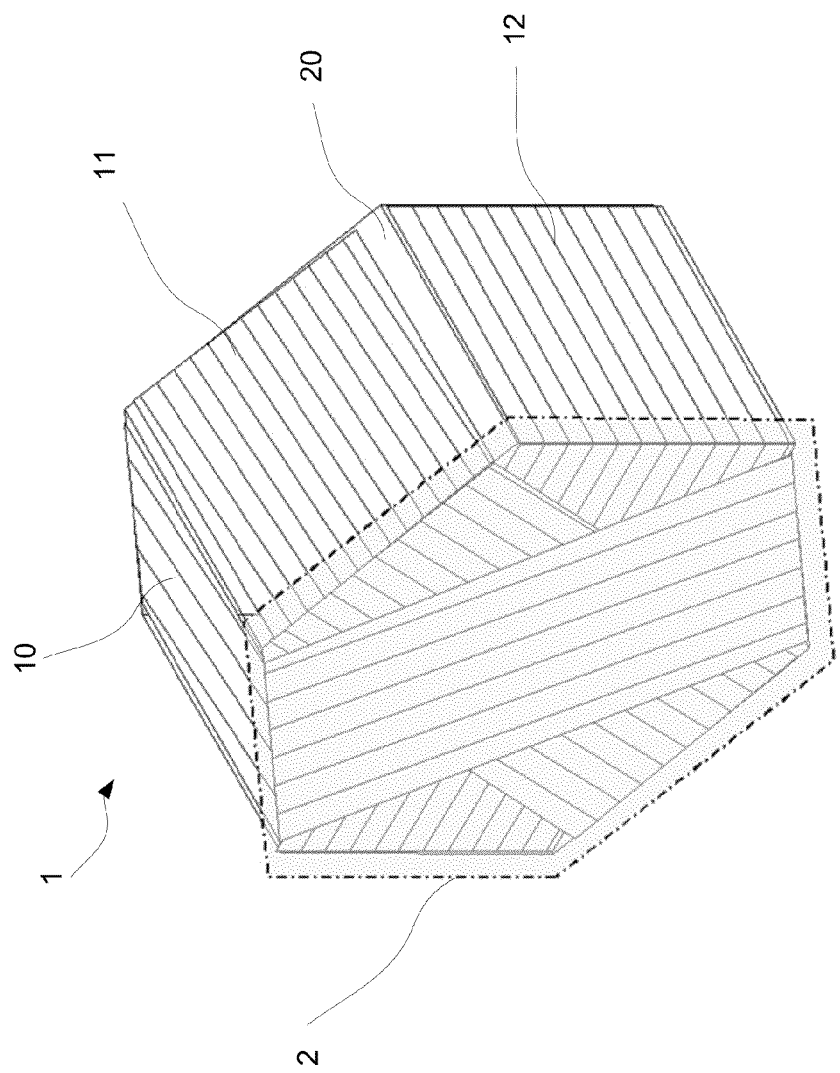
FIG. 1 is a schematic view of the multi-direction EC probe according to the present invention, showing a plurality of coils wrapped around the hexagonal core.

The preferred embodiment according to the present invention is a multi-directional probe as shown in FIG. 1. Referring to FIG. 1, the multi-directional probe 1 (herein also referred as "hexagonal probe") comprises one hexagonal core 20. Each of the three coils 10, 11 and 12 is wrapped around the hexagonal core 20, compassing the opposite faces of the hexagonal core 20. As a result, each coil 10, 11 or 12 is oriented at +/−60 degrees from each others. Probe 1 is designed to inspect a test surface 2 of a test object (not shown).

Figure 2:
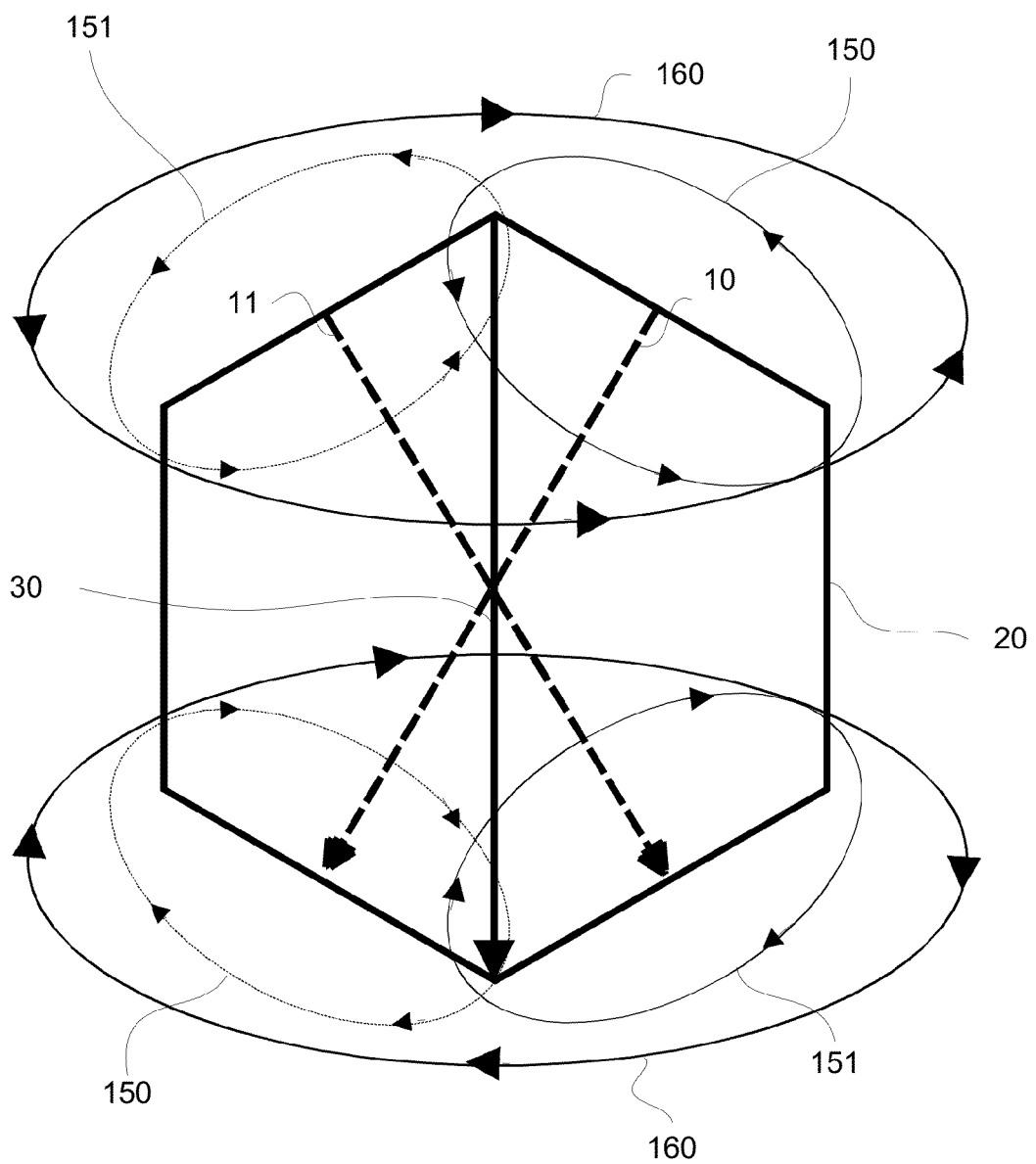
FIG. 2 is a schematic drawing showing the formation of the resulting magnetic field of two combined drivers, with 30-degrees phase shift from each other.

Collectively referring to FIGS. 1 and 2, for clarity of the drawings, coil 10 is represented by its main axis 10 and coil 11 is represented by its main axis 11 in FIG. 2. When an alternating current is injected in coil 10, an alternating magnetic field 150 is created around driver 10. Similarly, when an alternating current is applied in the driver coil 11, an alternating magnetic field 151 is created around driver 11. Since the two drivers 10 and 11 are provided with an alternating current in the same direction, the two emitted magnetic fields are circulating in the same direction and then it results in a combined magnetic field 160. The resulting magnetic field is equivalent to the magnetic field created by a driver oriented in the axis 30. Therefore, two drivers 10 and 11 can be combined and the result is an equivalent driver oriented in the axis 30.

The operation of hexagonal probe 1 herein described presents an important aspect of the present invention. A basic element of operating the hexagonal probe 1 is to electronically engage probe 1 in three separate steps, each at one of the three moments referred to as time intervals T1, T2 and T3, resulting in three different scanning channels, channel 1, channel 2 and channel 3. At each time interval, two of the three coils 10, 11, and 12 are used as emitters, and the third coil is used as receiver. At each time span, T1, T2 or T3, the two coils chosen to be the emitters and the coil chosen to be the receiver alternate. Since each of the three coils is shifted by 60 degrees with respect to the two other coils, the directional sensitivities of each channel rotates for each of the three resulting channels. The resulting and collective effect of the three channels allows for an inspection to cover any flaws with an orientation from 0 to 360 degrees, using the same probe with one run of scanning.

It should be noted that the three channels are not used at the same time because each coil needs to be either an emitter or receiver depending on the active channel. So, channels must be activated separately at different times. Synchronized activation of the suitable drivers and receivers is managed with a multiplexer able to switch the configuration at time spans T1, T2 or T3. A multiplexer suitable for such task is already commonly used in the industry and is not describe here in details. Also see later in FIG. 11 for the eddy current system including probe 1 and the multiplexer 1114.

Figure 3:
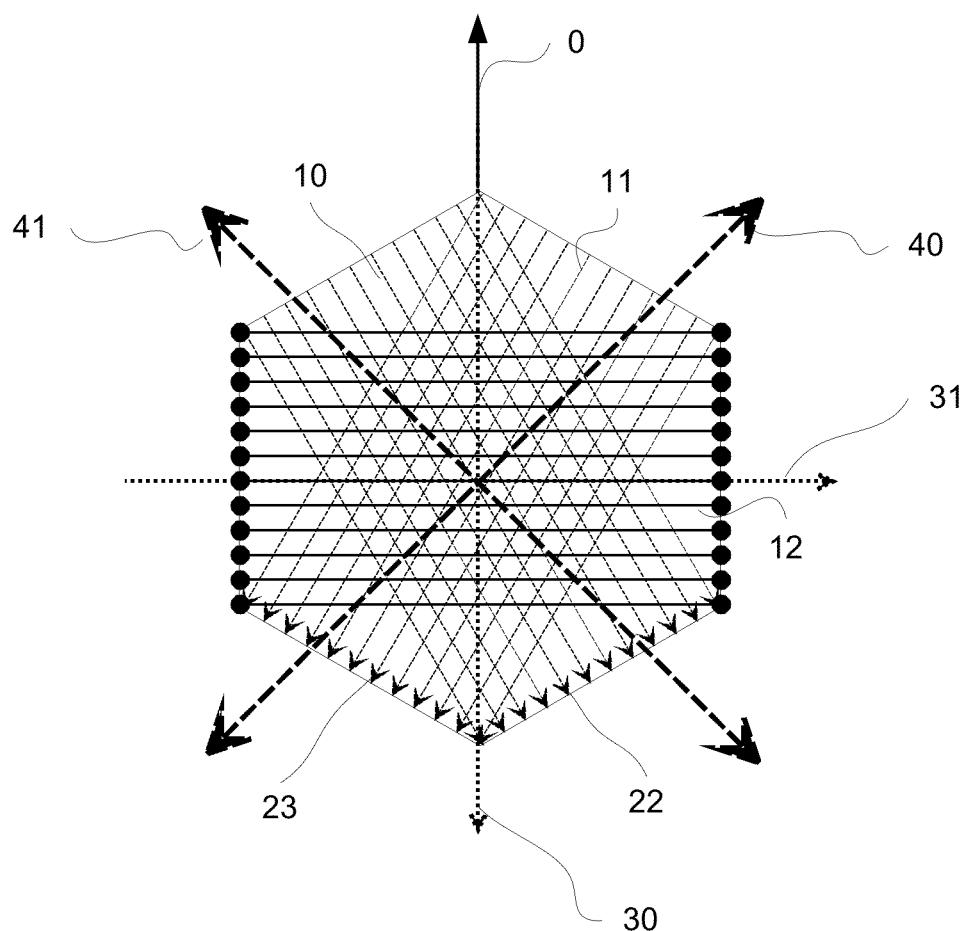
FIG. 3 is a diagram illustrating functionality of the hexagonal probe, for the channel 1 as example.

More specifically, referring to FIG. 3, alternating current is injected into coils 10 and 11 at time T1, respectively in the directions 22 and 23. The resulting or equivalent emitter of coils 10 and 11 is an emitter coil oriented and powered in the direction 30. Coil 12 is used as a receiver which is oriented in axis 31. Therefore, this hexagonal coil configuration at moment T1 is equivalent to a transmit-receive orthogonal probe in the background art, with an emitter oriented in axis 30 and the receiver oriented in axis 31. Such a probe configuration is the most sensitive to any cracks with a crack orientation at +/−45 degrees measured from the driver and receiver axes cores 30 and 31 respectively. More specifically, in an arbitrary reference plane, wherein the 0 degree position is defined by axis 0 in FIG. 3, the directional sensitivities of the hexagonal probe 1 with this inducing mode is at +45 deg and −135 deg, as shown on sensitivity orientation 40, and at −45 deg and +135 deg, as shown on orientation 41. The maximum EC response sensitivity reaches at orientations 40 and 41. The EC response sensitivity drops to substantially null at ±45° of orientations 40 and 41, or along axes 30 and 31.

Figure 4A:
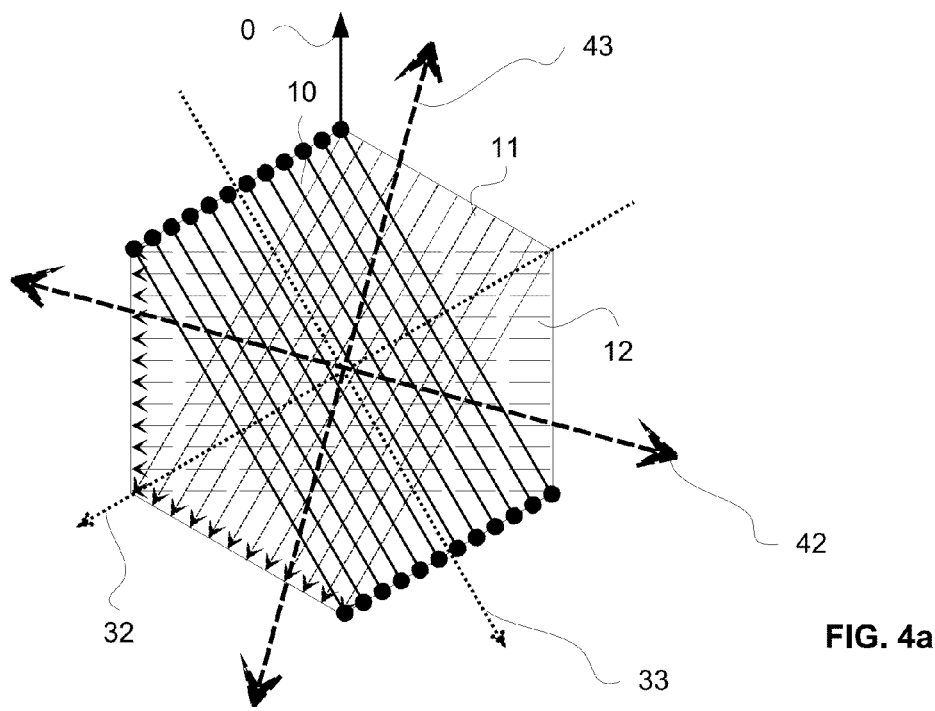
FIGS. 4a and 4b are diagrams illustrating functionality of the hexagonal probe, for the channels 2 and 3.

Referring now to FIG. 4a, at moment T2, the role of coils is rotated such that coil 10 becomes a receiver, oriented in axis 33, and coils 11 and 12 are simultaneously emitters. Similar to the operation sequence shown in FIG. 3 at moment T1, the resulting or equivalent emitter of coils 10 and 11 is an emitter coil oriented and powered in the direction 32. In an arbitrary reference plane, wherein the 0 degree position is defined by axis 0, the directional sensitivities of the hexagonal probe 1 at moment T2 is at +15 deg and −165 deg, as shown on sensitivity orientation 43, and at −75 deg and +105 deg, as shown on orientation 42. That is to say, at moment T2, probe 1 is the most sensitive to detect cracks with crack orientation closer to orientations 42 and 43. Probe 1 is the least sensitive to cracks with crack orientation close to or aligned with axes 32 and 33.

Figure 4B:
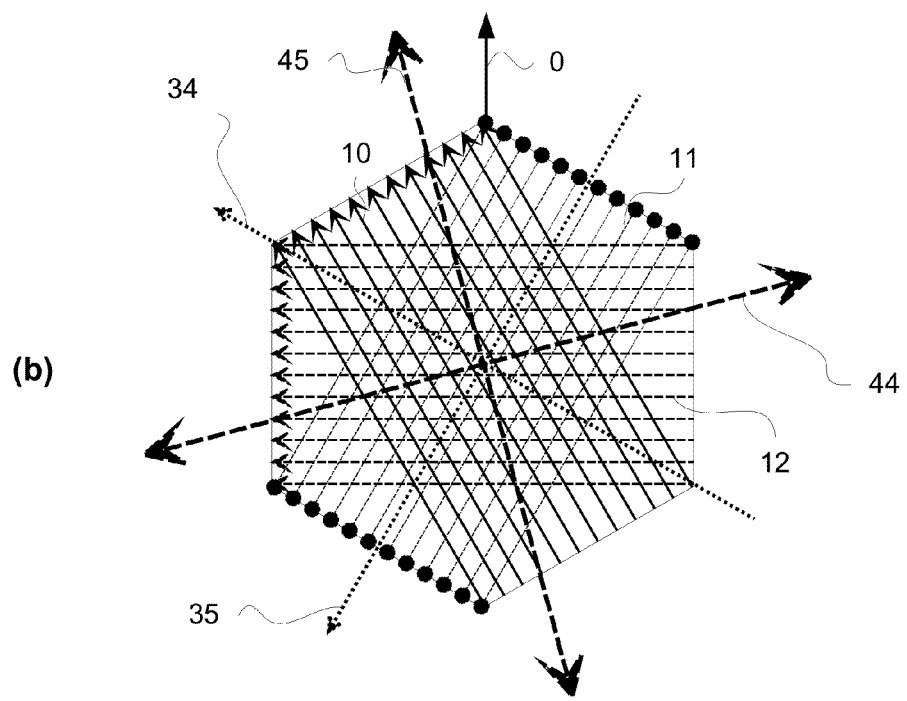

Referring to FIG. 4b, at moment T3, the role of coils is rotated such that coil 11 becomes a receiver, oriented in axis 35. Coils 10 and 12 are simultaneously emitters, resulting an emitter equivalent to an emitter oriented in direction 34. Such a probe configuration is the most sensitive to any cracks with crack orientation at +/−45 degrees of emitter or receiver axes 34 and 35. In an arbitrary reference plan, wherein the 0 degree position is defined by axis 0, the directional sensitivities of the hexagonal probe 1 with this configuration at +75 deg and −105 deg, as shown by axis 44, and at −15 deg and +165 deg, as shown by axis 45. That is to say, at moment T3, probe 1 is the most sensitive to detect cracks with crack orientation closer to orientations 44 and 45. Probe 1 is the least sensitive to cracks with crack orientation close to or aligned with axes 34 and 35.

Figure 5:
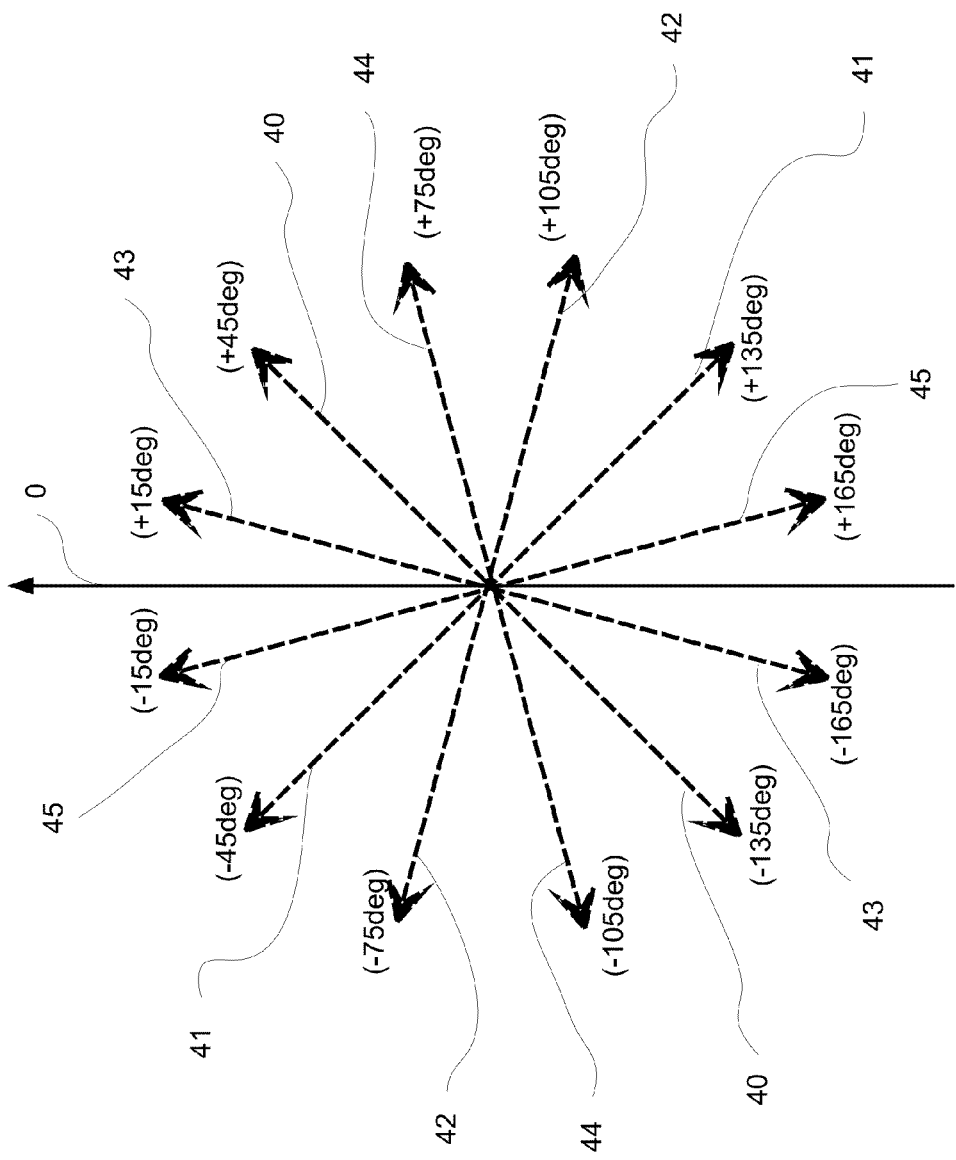
FIG. 5 is a diagram illustrating the optimum sensitivities axes of all the channels the hexagonal probe.

Reference is now turned to FIG. 5, which illustrates a merged sensitivity diagram of all of the three channels, as shown in FIGS. 3, 4a and 4b. As can be seen, probe 1 provides directional sensitivities from 0 to 360 degrees, with a phase shift of 30 degrees between each consecutive direction of sensitivity.

As can be seen in FIG. 5, since coils 10, 11 and 12 are substantially the same, hexagonal probe 1 is equivalent to the combination of three identical orthogonal EC probes staggered with an angular shift of 60 degrees from each other. Since the maximum sensitivity of all channels is substantially identical, a given flaw aligned with the directional sensitivity of any channel can be detected with the same signal amplitude. Therefore, flaws oriented at or close to angles of +/−15 deg, +/−45 deg, +/−75 deg, +/−105 deg, +/−135 deg and +/−165 deg, and substantially in the whole range of 360° on the test surface will be detected with sufficient sensitivity by one of the sensitivity channels.

Flaws oriented between two maximum sensitive directions are detected with relatively less sensitivity. For a given flaw, the more the flaw orientation differs from a maximum sensitivity direction, the smaller the amplitude signal obtained will be. For example, a 1 mm deep flaw at +45 deg could give a signal level approximately 2 dB higher than a 1 mm deep flaw oriented at +30 deg. However, since the probe of the present invention provides much more sensitive directions than prior art orthogonal probes, the overall sensitivity variation are minimized.

In addition, the flaw orientation is determined to be substantially the orientation of the inspection channel by which the largest amplitude response is received. Therefore the probe according to the present disclosure not only can detect similar flaws (in terms of depth and length) with constant sensitivity, but can also determine the orientation of the flaw.

Figure 6:
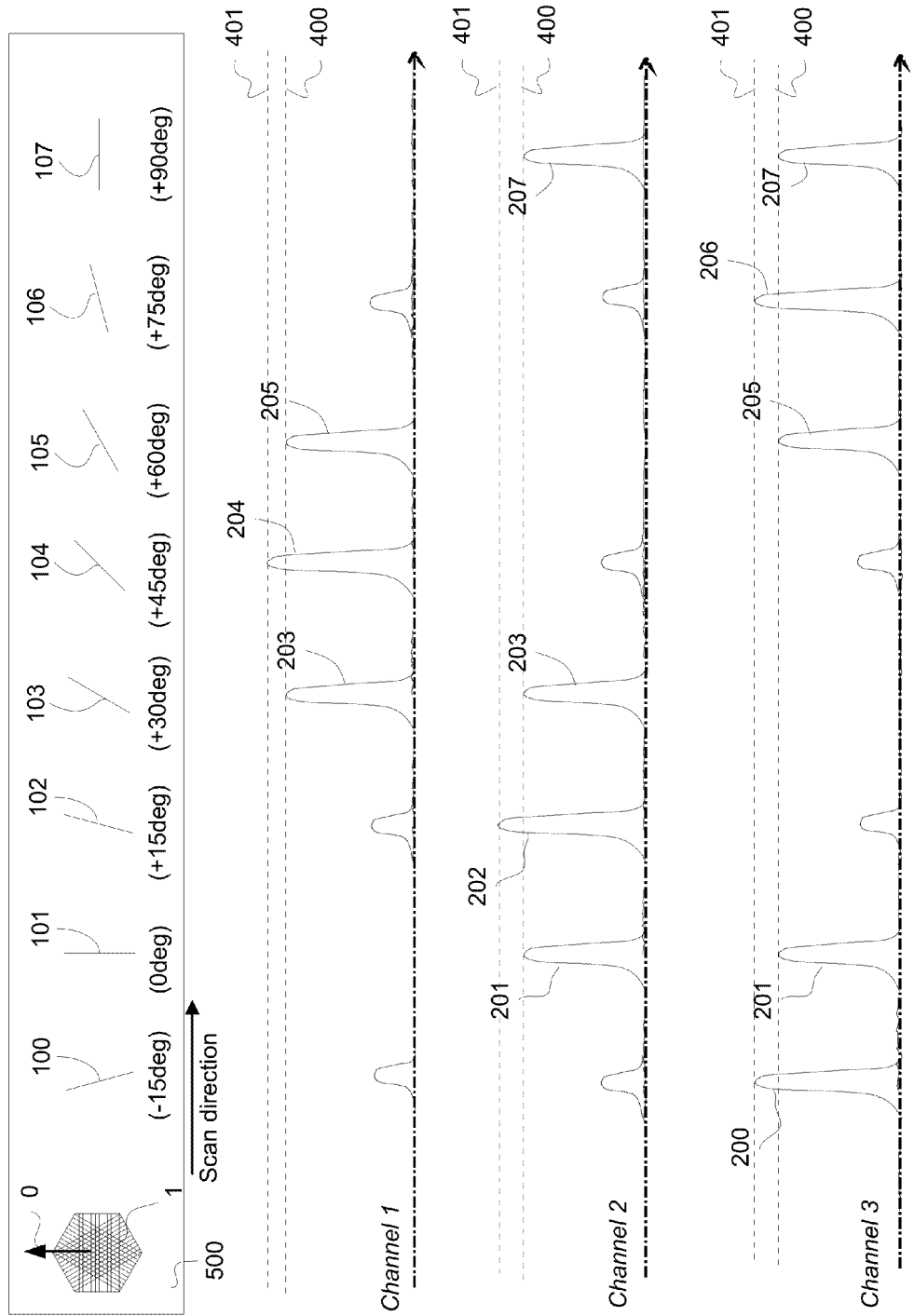
FIG. 6 is an illustration of the signal obtained with each channel of hexagonal probe for different flaw orientations.

Referring to FIG. 6, an exemplary session of inspection on test object 500 with plurality flaws (100, 101, . . . 107) oriented from −15 deg to +105 deg is described as follows. Exemplary channels 1, channel 2 and channel 3 continue to be used to refer to the three pairs of inspection sensitive regions when the three coils are alternatively engaged as described in FIGS. 3, 4a and 4b.

Flaw 100 oriented at −15 deg is detected by the multi-directional probe 1. The detection of flaw 100 is shown by all channels 1, 2 and 3, with depicted amplitudes 200-207. However, the maximum signal amplitude 200 is received from channel 3 since the flaw is perfectly aligned with channel 3 sensitivity axis. Line 401 represents the maximum amplitude detected by hexagonal probe 1.

A minimum response amplitude of a flaw is predetermined according to the specific requirements of an inspection. For instance, an amplitude response between maximum 401 and minimum 400 is considered to indicate the presence of a flaw. The minimum flaw amplitude is defined to cover the "worst situation". That is to say minimum amplitude is defined as a response amplitude received from minimally allowed crack sizes and depths with orientations at which the probe presents the weakest sensitivity.

Similar results are obtained for flaws 102, 104 and 106, oriented respectively at +15 deg, +45 deg, +75 deg and respectively detected by the channels 2, 1, 3. The amplitude of detection of those flaws reaches the maximum amplitude 401 of the hexagonal probe 1.

Continuing with FIG. 6, flaw 101 oriented at 0 deg is detected by only two of the three channels, and the signal amplitude 201 is detected from both of channels. This is because the flaw orientation is exactly between the sensitivity axis of channels 2 and 3. The amplitude of detection reaches a predetermined acceptable minimum amplitude 400.

Similar results are obtained with flaws 103, 105, 107, oriented respectively +30 deg, +60 deg, +90 deg and detected respectively by channels 1 and 2, channels 1 and 3 and channels 2 and 3. The amplitude of detection of those flaws reaches the minimum amplitude 400 the hexagonal probe 1, providing the basis for reporting 103, 105 and 107 as flaws.

Figure 7:
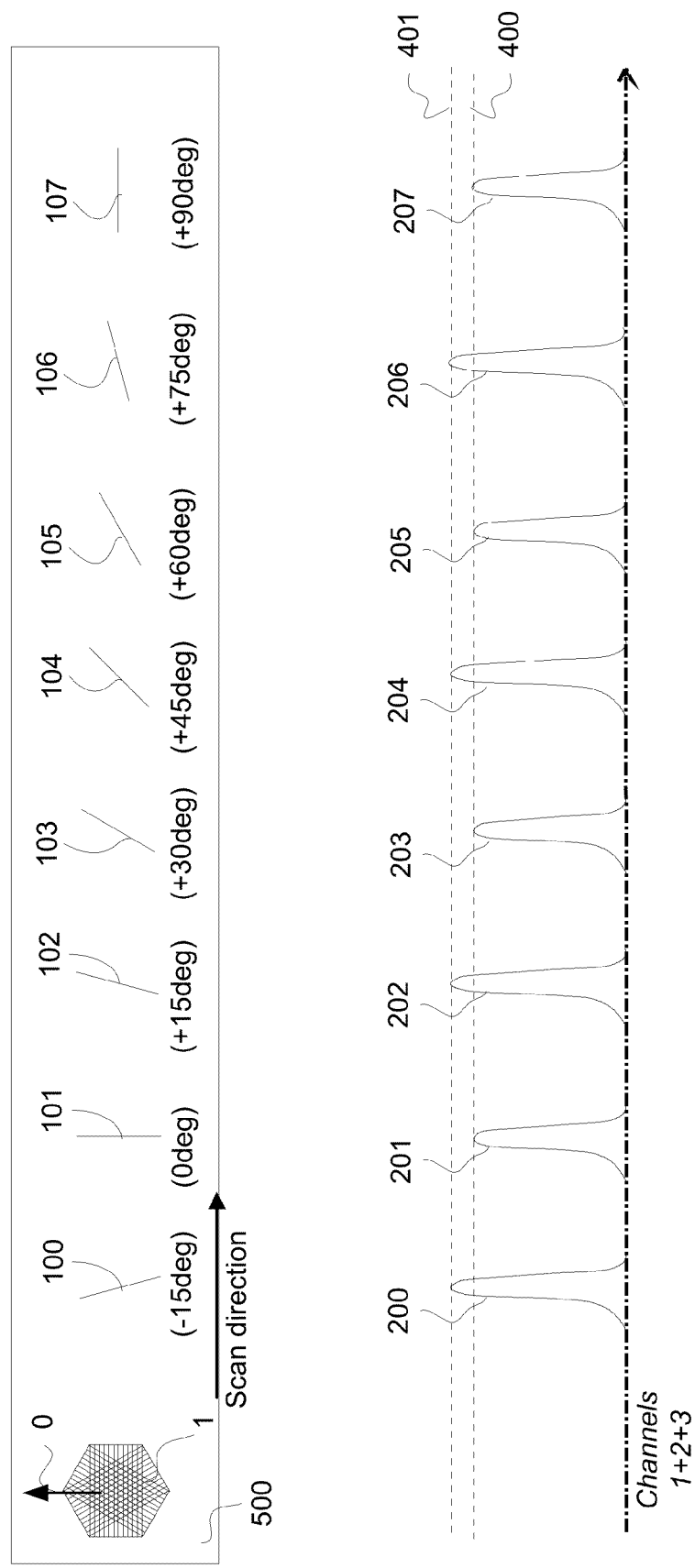
FIG. 7 is an illustration of the merged signals of the 3 channels obtained with hexagonal probe, for different flaws orientation.

Moving on to FIG. 7, the maximum amplitudes from each of the three channels of the hexagonal probe 1 are combined. The collective reading of the amplitudes presents that the detection of eight flaws oriented between −15 deg and +90 deg. During this exemplary inspection, all the flaws with the same specification (depth, width, length), except the orientation, 100, 101, 102, 103, 104, 105, 106, 107, are detected by the hexagonal probe 1 with amplitude reading between maximum 401 and minimum 400.

The maximum and minimum signal levels can change depending on the depth of the flaw and the flaw orientation. The deeper the flaws, the higher the maximum signal is detected at one specific flaw orientation. One can appreciate that the amplitude of a deeper flaw at angles 0 deg, +30 deg or +60 deg may have the same amplitude reading as those from a shallower flaw at angles +15 deg, +45 deg or +75 deg.

Figure 8:
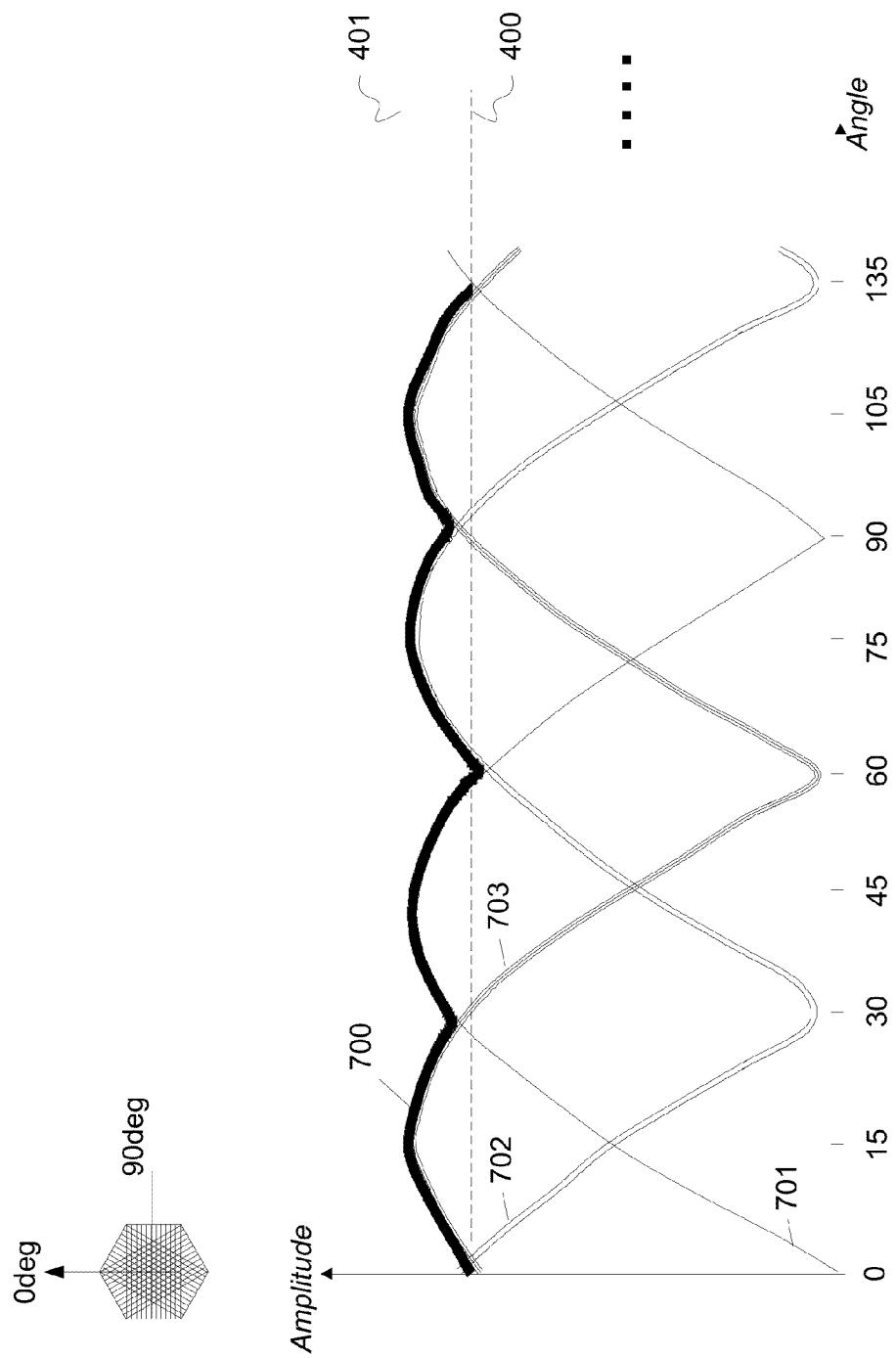
FIG. 8 is the overall sensitivity response of the hexagonal probe for all orientations 0-360 deg.

Turning now to FIG. 8, the resultant sensitivity response from all three coils of hexagonal probe 1 is detailed in the diagram. The sensitivity of channel 1 is shown by curve 701 reaching a maximum at +45 deg and minima at 0 and +90 deg. The sensitivity of channel 2 is shown by curve 702 reaching a maximum at +75 deg and minima at +30 deg and +135 deg. The sensitivity of channel 3 is shown by curve 703 reaching maxima at +15 deg and +105 deg and a minimum at +60 deg. The merge of the maximum of each of the three channels is shown with curve 700, with maxima at +15 deg, +45 deg, +75 deg, and the minima are defined by the junction between individual channels at +30 deg, +60 deg, +90 deg. The minimum and maximum amplitudes of hexagonal probe sensitivity curve 700 are between maximum detection amplitude 401 and minimum detection amplitude 400.

Figure 9:
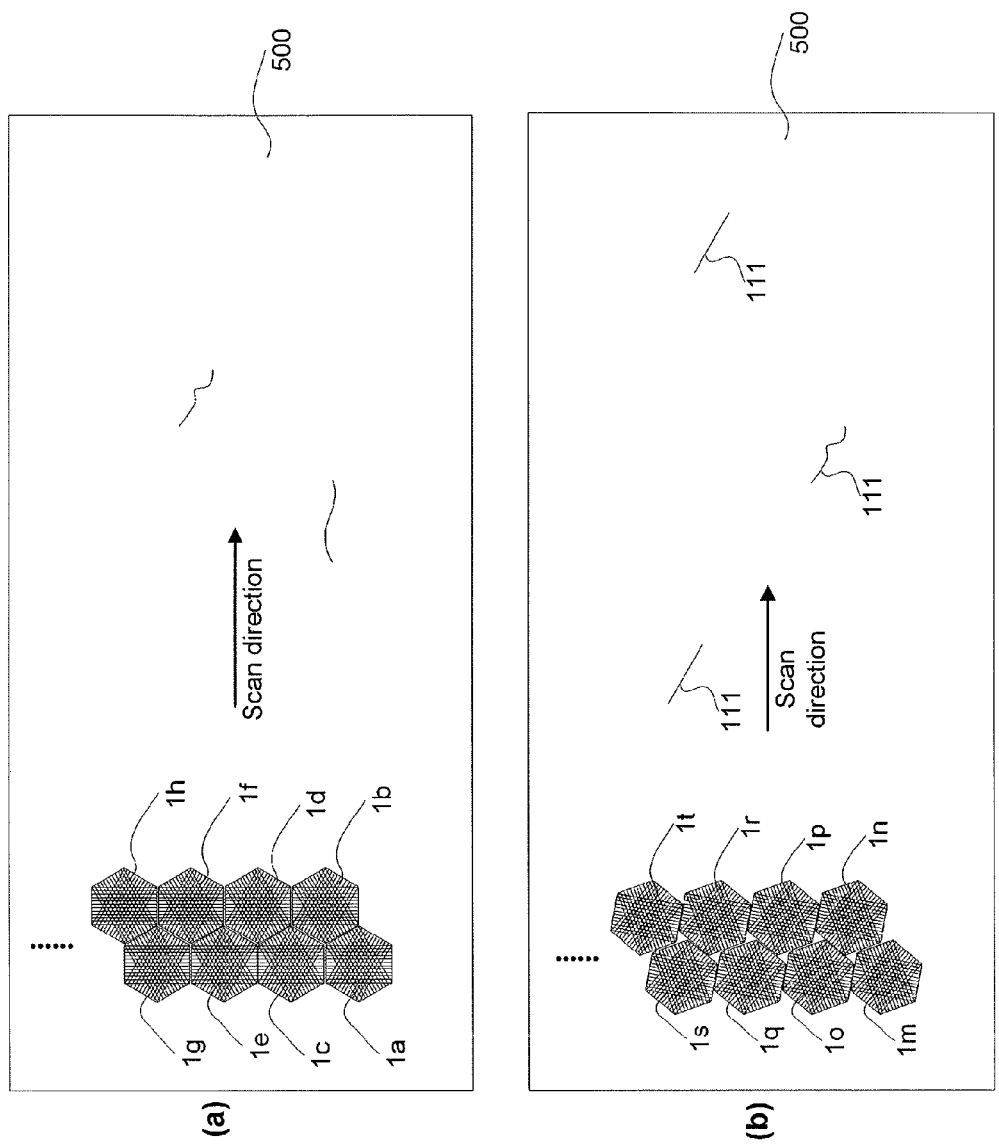
FIGS. 9a and 9b illustrate an alternative embodiment of the hexagonal probe in an array configuration.
Figure 10:
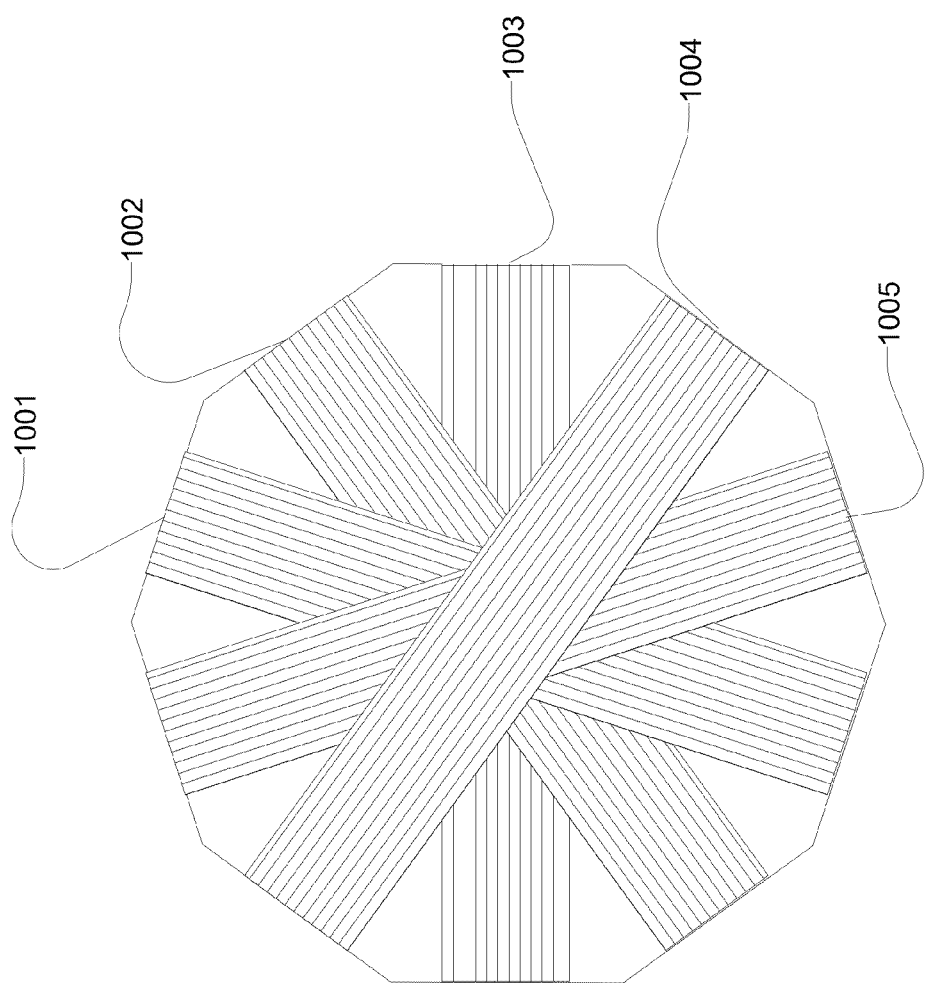
FIG. 10 illustrates another alternative embodiment with five coils wound on a decagonal block.

Next, a few alternative embodiments are described in association with FIGS. 9a, 9b and 10. It should be noted that the description of the alternative embodiments should be construed complementally to the preferred embodiment. The description of the alternative embodiments focuses on the variation from the main (preferred) embodiment, instead of being complete.

Referring to FIG. 9a, an alternative embodiment of the hexagonal probe is shown to be assembled in an array configuration. One should appreciate the easiness of such combination of the hexagonal probe according to the present invention, such that a wider range of scan can be achieved with higher productivity. As seen in FIG. 9a, hexagonal probes 1a to 1f or more can be staggered for optimum inspection coverage of test object 500. The design of the array probe largely depends on the limitation of number of channels provided by the acquisition unit (not shown).

It should be noted that, under most situations, the potential defects are anticipated to occur in some most expected orientation. Referring to FIG. 9b, the orientation of the hexagonal probes according to the present invention can therefore be optimized for the detection of some anticipated flaws. For example, a component known to have 30 degrees flaws 111, created by a specific step of the manufacturing process, could be scanned with an array of the multi-directional probes rotated with +15 deg as shown in FIG. 9b, as probes 1m to 1t. In this way, the directional sensitivity of the hexagonal probe is preferably aligned with the most frequently existing flaws on test object 500.

The scope of the present invention can be extended to many kinds of polygonal prisms, allowing a combination of drivers, resulting in one equivalent driver, perpendicular to receiver axis.

For example, the multi-directional probe could be extended to take shape with 10 sides (decagon), in order to increase the number of directional sensitivities of the probe. Referring to FIG. 10, a decagon probe comprises 5 coils, 1001, 1002, 1003, 1004, and 1005. For this embodiment, any coil-grouping configurations that causes resultant driver axis to orthogonal to receiver axis can be used. For example, referring to FIG. 10, one of the following three coil-grouping configurations can be used for an inspection setting. 1) Coils 1001 and 1005 are used as drivers when coil 1003 is used as receiver. A corresponding arrangement is used to form a pattern of alternating the roles of coils during subsequent inducing-sensing sequence. 2) Coils 1002 and 1004 are used as drivers when coil 1003 is used as receiver. A corresponding arrangement is used to form a pattern of alternating the roles of coils during subsequent inducing-sensing sequence. 3) Coils 1001, 1002 and 1004, 1005 could be used as drivers when coil 1003 is used as receiver. Similarly, a corresponding arrangement is used to form a pattern of alternating the roles of coils during subsequent inducing-sensing sequence. One can appreciate that the above three configurations share the same attribute which is to provide a resultant driver EC field, of which the axes are perpendicular to the receiver axes. Therefore the probe in this alternative embodiment provides the capability of inspecting flaws of all orientations, with the least noise to signal ratios.

Figure 11:
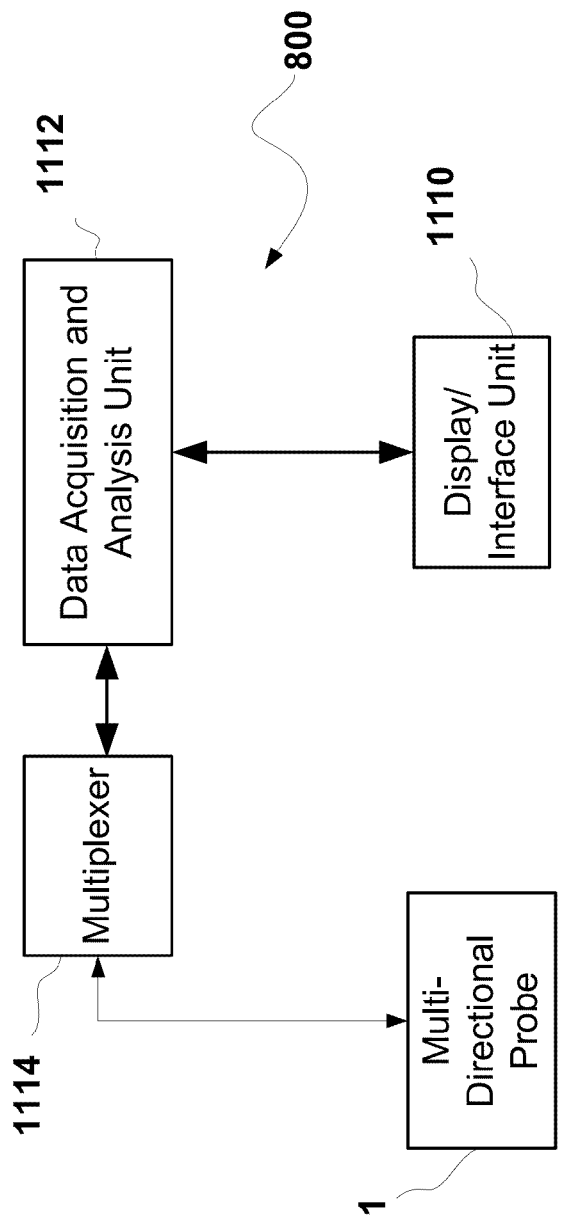
FIG. 11 is a system block diagram of the invention.

It should be noted that existing eddy current systems, such as system 800 as shown in FIG. 11 can be used with the presently disclosed probe 1. As shown in FIG. 11, system 800 preferably includes multiplexer 1114, a data acquisition and analyzing unit 1112 and a display/interface unit 1110.

Although the present invention has been described in relation to particular exemplary embodiments thereof, many other variations and modifications and other uses will become apparent to those skilled in the art. It is preferred, therefore, that the present invention not be limited by the specific disclosure.

The hexagonal probe according to the preferred embodiment can be made into three pairs of two-dimensional (2D) eddy current coils, resulting in a similar eddy current response and inspection results. The method of converting to such 2D configuration is detailed by U.S. application Ser. No. 12/832,620, the entire content of which is herein incorporated by reference.

What is claimed is:

1. An eddy current system having at least one eddy current probe configured for inspecting a test object for flaws of any flaw orientation, wherein the probe comprises:
    at least three coils, each of the coils is wound across two facing sides of an at least six-sided right polygonal prism,
    wherein at a finite time interval, at least two of the coils are configured to be eddy current driver coils, being charged simultaneously with electric current driven in coherent directions to induce predetermined eddy currents and one of the coils is configured to be an eddy current receiver coil to sense the eddy current,
    wherein the eddy currents induced by the at least two driver coils form a combined eddy current, the axis of the combined eddy current is orthogonal to the axis of the receiver coil,
    wherein each coil alternates to be one of the driver coils or the receiver coil at a predetermined switching sequence during consecutive time intervals; and,
    during the inspection of the test object, the probe is configured to be moved over a test surface with one polygonal prism base face facing the test surface.

2. The eddy current system in claim 1, wherein the probe is configured to diagnose flaws of any flaw orientation with the probe passing over the test surface with one pass of scan.

3. The eddy current system in claim 1, wherein the polygonal prism is an electrically non-conductive core.

4. The eddy current system in claim 1, wherein the probe is most sensitive to flaws with a plurality of predetermined orientations.

5. The eddy current system in claim 4, wherein the probe is oriented in a scanning path in such a way that the most sensitive orientation of the probe is aligned with an anticipated flaw orientation.

6. The eddy current system in claim 1, wherein the system defines predetermined threshold of flaws with predetermined physical characteristics, the threshold being determined when flaws with the predetermined physical characteristics being detected with the least sensitivity.

7. The eddy current system in claim 1, wherein a combination of the at least two driver coils and the receiver coil forms an inspection channel.

8. The eddy current system in claim 7, wherein the flaw orientation is determined to be substantially the orientation of the inspection channel from which the largest amplitude response is received.

9. The eddy current system in claim 7, further comprising,
    a multiplexer operable to induce and receive signals from different channels at different time intervals at the predetermined switching sequence and a predetermined switching frequency,
    a data analyzing and storage unit,
    a display unit.

10. The eddy current system in claim 1, wherein the time intervals are substantially equal.

11. The eddy current system in claim 1, wherein the at least three coils are substantially the same.

12. The eddy current system in claim 1, wherein the polygonal prism is a hexagonal prism.

13. The eddy current system in claim 1, wherein the polygonal prism is a decagonal prism.

14. The eddy current system in claim 13, wherein when 0 angular degree is defined as the axis of the receiver coil, the probe is most sensitive to flaws with flaw orientations of angular degrees of +/−15, +/−45, +/−75, +/−105, +/−135 and +/−165; and, the probe is the least sensitive to the flaws with flaw orientations of angular degrees of 0, +/−30, +/−60, +/−90, +/−120, +/−150 and 180.

15. The eddy current system in claim 1, wherein the system comprises an array of the probes arranged in a staggered fashion to cover wider range of the test surface in one scanning path.

16. The eddy current system of claim 1, wherein said coils are alternated at a predetermined switching frequency.

\* \* \* \* \*